US00PP23374P2

(12) United States Plant Patent
NeSmith et al.

(10) Patent No.: US PP23,374 P2
(45) Date of Patent: Feb. 5, 2013

(54) BLUEBERRY HYBRID PLANT NAMED 'T-885'

(50) Latin Name: ***Vaccinium* sp.**
Varietal Denomination: T-885

(75) Inventors: D. Scott NeSmith, Molena, GA (US); Mark K. Ehlenfeldt, Tabernacle, NJ (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 13/317,178

(22) Filed: Oct. 11, 2011

(51) Int. Cl.
*A01H 5/00* (2006.01)

(52) U.S. Cl. ..... Plt./157

(58) Field of Classification Search ..... Plt./157
See application file for complete search history.

*Primary Examiner* — Annette Para
(74) *Attorney, Agent, or Firm* — Klarquist Sparkman, LLP

(57) ABSTRACT

The variety 'T-885' ripens around the first week of June in southern Georgia. The fruit of the new variety 'T-885' are generally small. The fruit of the new 'T-885' variety ripens progressively and not all at once creating multiple-colored fruit clusters. The new 'T-885' variety is highly vigorous with an estimated chilling requirement of about 500 to 550 hours at or below approximately 7° C. The variety is reliably propagated vegetatively.

3 Drawing Sheets

STATEMENT REGARDING FEDERALLY-SPONSORED RESEARCH

This invention was made in parts with U.S. Government support on behalf of U.S. Department of Agriculture, Hatch Act Grant No. GEO 01663. The U.S. Government has certain rights in this invention.

Latin name of the genus and species of the plant claimed: 'T-885' is a new blueberry hybrid plant that is a *Vaccinium* sp. hybrid.

Variety denomination: The new blueberry hybrid plant claimed is a new cultivar denominated 'T-885'.

BACKGROUND OF THE INVENTION

The present invention relates to the discovery of a new and distinct cultivar of blueberry hybrid plant botanically known as a *Vaccinium* sp. hybrid and herein referred to as 'T-885', as herein described and illustrated. The blueberry plant contains mostly rabbiteye germplasm.

The new blueberry plant variety 'T-885' was selected while growing in a cultivated area in Griffin, Ga. in 2005. The new variety 'T-885' ripens around the first week of June in southern Georgia. The fruit of the new variety 'T-885' are generally small to medium size. The new variety's fruit ripens progressively and not all at once, creating multiple colored fruit clusters. The new variety 'T-885' is highly vigorous with an estimated chilling requirement of about 500 to 550 hours at or below approximately 7° C.

Pedigree and history—The new blueberry plant variety 'T-885' was selected in 2005 at the Georgia Experiment Station in Griffin, Ga. It originated from a cross of 'Climax' X US 1056. 'Climax' (unpatented) is an older standard rabbiteye cultivar (*V. ashei*), while US 1056 is an unpatented breeding line with a complex pedigree containing *V. ashei, V constablaei, V. corymbosum,* and *V. darrowii*. The selection has been asexually propagated by softwood cuttings in Alapaha and Griffin Ga. The new cultivar has been tested in plantings at Alapaha and Griffin, Ga. since 2006.

The new 'T-885' blueberry plant has been shown to maintain its distinguishing characteristics through successive asexual propagations by softwood cuttings. Plants from softwood cuttings have been directly planted in the ground.

SUMMARY OF THE INVENTION

'T-885' has not been observed under all possible environmental conditions. The phenotype may vary somewhat with variations in environment and cultural practices such as temperature and light intensity without, however, any variance in genotype.

The following traits have been repeatedly observed in 'T-885' plants growing in Alapaha and Griffin Ga., and are determined to be the unique characteristics of 'T-885' plants:

1. Excellent plant vigor;
2. Firm fruit;
3. Fruit ripening progresses through several colors.

The new variety 'T-885' has been compared to the rabbiteye blueberry varieties 'Climax', and 'Premier' (unpatented).

Comparison to 'Climax' and 'Premier': The new variety 'T-885' has limited commercial production value, but rather features unique multi-colored berries and non-glaucous foliage, making it an attractive plant for ornamental purposes. The new variety is a vigorous blueberry plant having fruit that ripen around the time of the older rabbiteye blueberry standard cultivars, 'Climax' and 'Premier', which are both considered to be vigorous cultivars with early ripening berries. Comparison fruit and plant data are listed in Tables 1 and 2 as follows.

TABLE 1

Average fruit and plant ratings of 'T-885' and two rabbiteye (Climax and Premier) standard cultivars over a 2 year period (2008-2009) at Alapaha, GA. Rating scales are based on a 1 to 10 score, with 1 being the least desirable and 10 being the most desirable for a commercial blueberry variety. Values in rows followed by the same lower case letter are not significantly different.

| Berry and plant attribute | T-885 | Climax | Premier |
|---|---|---|---|
| Berry size | 6.8 b | 6.8 b | 7.8 a |
| Berry scar | 7.0 b | 7.8 a | 7.8 a |
| Berry color | 4.5 b | 7.0 a | 7.8 a |

TABLE 1-continued

Average fruit and plant ratings of 'T-885' and two rabbiteye (Climax and Premier) standard cultivars over a 2 year period (2008-2009) at Alapaha, GA. Rating scales are based on a 1 to 10 score, with 1 being the least desirable and 10 being the most desirable for a commercial blueberry variety. Values in rows followed by the same lower case letter are not significantly different.

| Berry and plant attribute | T-885 | Climax | Premier |
|---|---|---|---|
| Berry firmness | 7.0 ab | 7.6 a | 6.8 b |
| Berry flavor | 7.0 a | 7.3 a | 7.8 a |
| Crop load | 5.0 ab | 6.0 a | 4.0 b |
| Plant vigor | 8.8 a | 6.7 b | 9.3 a |
| Date of 50% flowering | March 23 | March 14 | March 21 |
| Date of 50% ripening | June 5 | June 3 | June 3 |

TABLE 2

Average fruit and plant ratings of T-885 and two rabbiteye (Climax and Premier) standard cultivars over a 2 year period (2008-2009) at Griffin, GA. Rating scales are based on a 1 to 10 score, with 1 being the least desirable and 10 being the most desirable for a commercial blueberry variety. Values in rows followed by the same lower case letter are not significantly different.

| Berry and plant attribute | T-885 | Climax | Premier |
|---|---|---|---|
| Berry size | 6.3 b | 6.9 b | 7.7 a |
| Berry scar | 7.2 a | 7.5 a | 7.5 a |
| Berry color | 4.0 b | 7.2 a | 7.5 a |
| Berry firmness | 6.5 b | 8.0 a | 6.8 b |
| Berry Flavor | 7.0 a | 7.2 a | 7.2 a |
| Crop load | 6.0 a | 5.5 a | 3.5 b |
| Plant vigor | 8.0 a | 7.6 ab | 7.0 b |
| Date of 50% flowering | March 28 | March 23 | March 28 |
| Date of 50% ripening | June 24 | June 17 | June 16 |

BRIEF DESCRIPTION OF THE FIGURES

The accompanying photographic illustration shows typical specimens in full color of the foliage and fruit of the new variety 'T-885'. The colors are as nearly true as is reasonably possible in a color representation of this type.

The colors of an illustration of this type may vary with lighting and other conditions. Therefore, color characteristics of this new variety should be determined with reference to the observations described herein, rather than from these illustrations alone.

BOTANICAL DESCRIPTION

Figure 1:
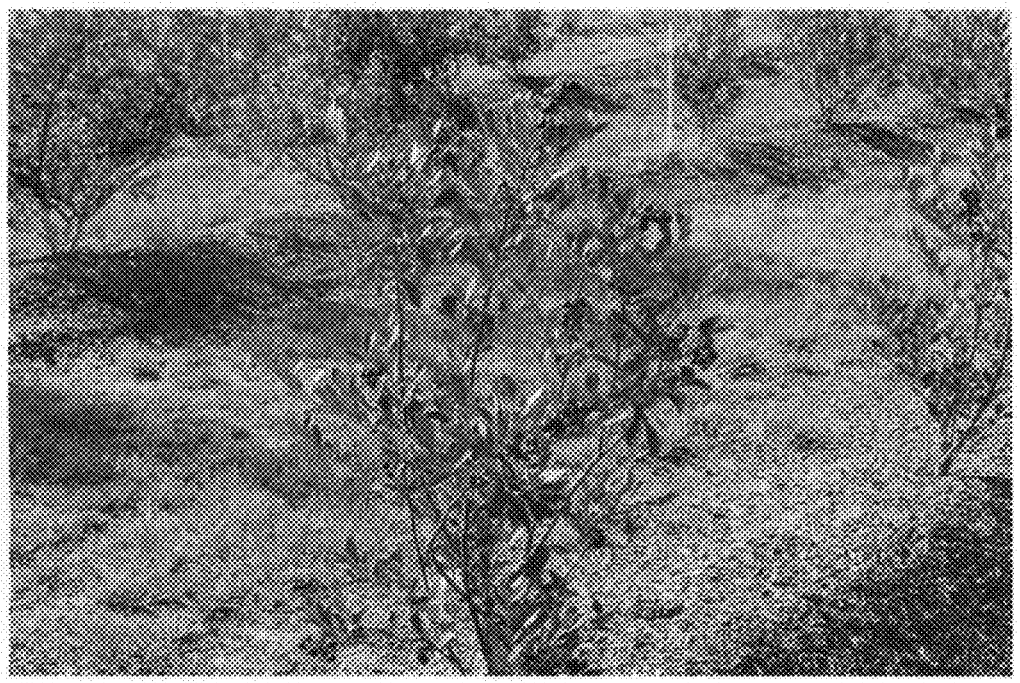
FIG. 1 is a photograph of a two year old 'T-885' plant growing in Alaphaha, Ga., taken during June of 2008.
Figure 2:
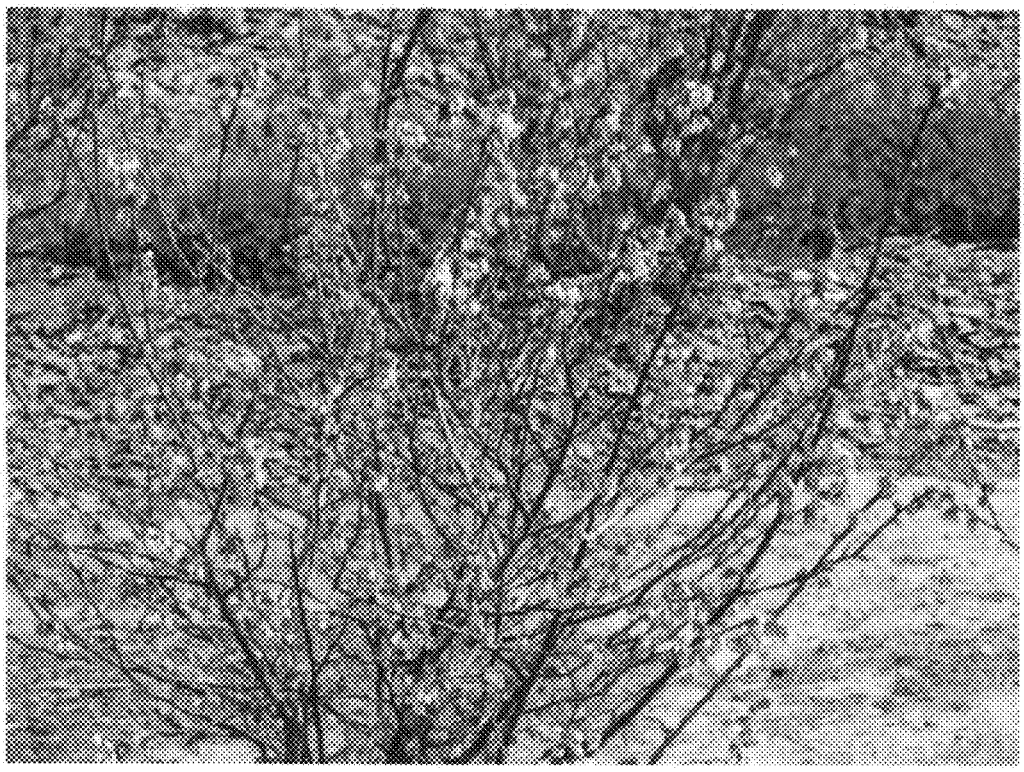
FIG. 2 is a photograph of a 'T-885' plant growing in Griffin, Ga. during flowering.
Figure 3:
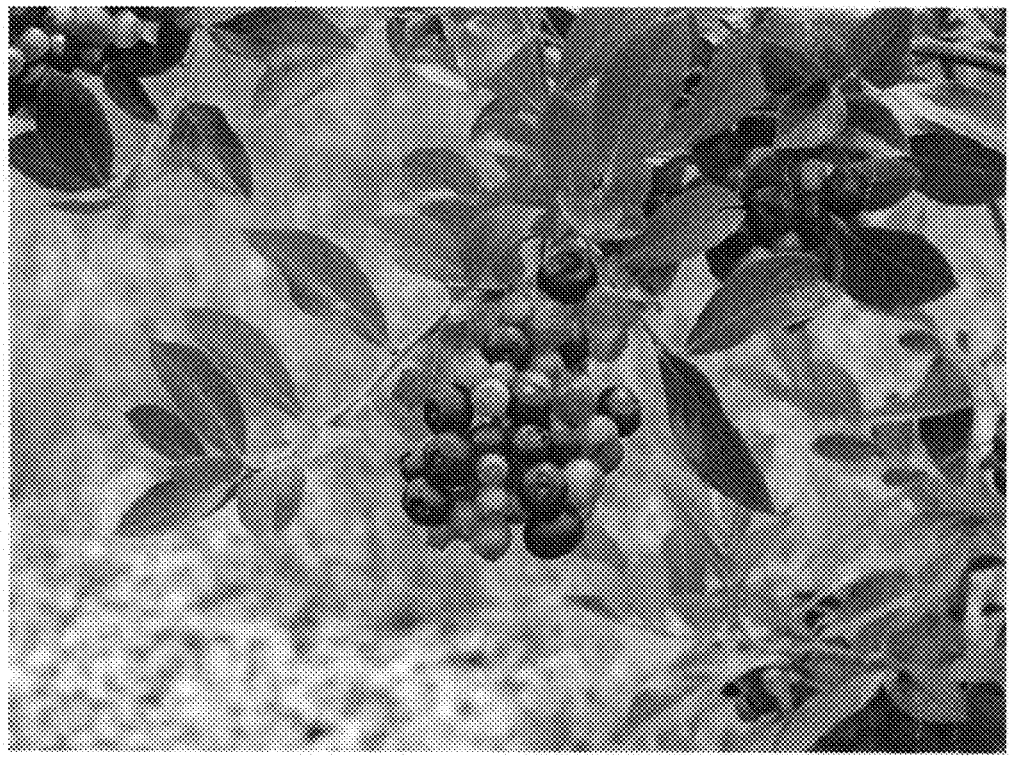
FIG. 3 is a close-up photograph of the fruit and foliage of a 'T-885' plant showing the non-uniform ripening of the fruit.

Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society, London, England.

The following is a detailed description of the botanical and pomological characteristics of the new variety 'T-885'. Where dimensions, sizes, colors, and other characteristics are given, it is to be understood that such characteristics are approximations and averages set forth as accurately as practicable. The descriptions reported herein are largely from specimen plants that were about 3 to about 4 years old grown in Alapaha and Griffin, Ga., with supplemental irrigation.

PLANT

Parentage: 'Climax'×U.S. 1056.

Size: 1.0 to 1.2 m tall by about 3 years of age with an upper canopy of 1 m wide.

Growth habit: Upright to semi-spreading with 2 to 5 canes arising from the crown with immediate branching.

Growth: Highly vigorous.

Productivity: Medium, averaging 4 to 6 lbs per plant each year for 3 to 4 year old plants grown in bark beds with supplemental irrigation.

Hardiness: Similar to other rabbiteye cultivars such as 'Climax' and 'Premier'.

Chilling requirement: 500 to 550 hours of temperatures at or below about 7° C. (about 45° F.) to induce normal leafing and flowering during the spring.

Leafing: Plants readily break numerous leaf buds simultaneously with anthesis.

Canes:

*Diameter.*—25 to 35 mm in plants that are about 3 years old and older. 7 to 10 mm in about 2 year old wood. 3 to 4 mm on current season wood.

*Color.*—Greyed-Green RHS 197C in plants that are about 3 years old and older. Yellow-Green RHS 144B transitioning to about Greyed-red RHS 178B to Greyed-purple RHS 183A in about 2 year old wood. Yellow-green RHS 145A to Greyed-red RHS 178B on current season wood.

FOLIAGE

Leaf color: Healthy mature leaves.

*Top side.*—Green RHS 137A.

*Under side.*—Green RHS 138B.

Leaf arrangement: Alternate, simple.

Leaf shape: Elliptic.

Leaf margins: Serrate to serrulate.

Leaf venation: Reticulate.

Leaf apices: Acute.

Leaf bases: Acute.

Leaf dimensions:

*Length.*—50 to 60 mm.

*Width.*—20 to 25 mm.

Petioles: Small.

*Length.*—3.0 to 4.0 mm.

*Width.*—1.5 to 2.0 mm.

*Color.*—Yellow-Green RHS 145C.

FLOWERS

Date of 50% anthesis: March 23 (2 year average) in southeast Georgia; March 28 (2 year average) in middle Georgia.

Flower shape: Urceolate.

Flower bud number: High.

Flowers per cluster: 7 to 9.

Flower fragrance: None.

Corolla:

*Color.*—White N155D (open flower).

*Length.*—6.5 to 7.5 mm.

*Width.*—5.5 to 6.5 mm.

*Aperture width.*—3.0 to 3.5 mm.

Flower peduncle:
*Length.*—9.0 to 11.0 mm.
*Color.—Yellow-Green RHS* 146C.
Flower pedicle:
*Length.*—5.0 to 6.5 mm.
*Color.*—Yellow-Green RHS 146D.
Calyx (with sepals):
*Diameter.*—6.0 to 6.5 mm.
*Color* (*sepals*).—Green RHS 139C.
Stamen:
*Length.*—7.0 to 8.0 mm.
*Number per flower.*—10.
*Filament color*.—Yellow-Green RHS 145D.
Style:
*Length.*—8.0 to 10.0 mm.
*Color*.—Yellow-Green RHS 145C.
Pistil:
*Length.*—9.0 to 12.0 mm.
*Ovary color* (*exterior*).—Green RHS 137C.
Anther:
*Length.*—4.0 to 5.0 mm.
*Number.*—10.
*Color*.—Greyed-Orange RHS 165B.
Pollen:
*Abundance*.—Medium.
*Color*.—Yellow-white RHS 158A.
Self-compatibility: The cultivar has demonstrated a low degree of self-compatibility.

FRUIT

Date of 50% maturity: June 5 (2 year average) in southeast Georgia; June 24 (2 year average) in middle Georgia.
Fruit development period: 75 to 85 days.
Berry color: Berries are non-waxy, and progress through several colors as they ripen. Typical color transitions are Green 145B, going to Orange-red 33B, going to Red 46A, going to Greyed-purple 187B, finally going to Black 202A at maturity.
Berry surface wax abundance: Very low to none.
Berry flesh color: Green-white RHS 157A.
Berry weight:
*First harvest.*—1.0 g to 1.2 g.
*Second harvest.*—0.8 g to 1.0 g.
Berry size:
*Height from calyx to scar.*—10.0 to 12.0 mm.
*Diameter.*—8.0 to 10.0 mm.
Berry shape: Spherical.
Fruit stem scar: Medium, dry, no tearing.
Berry firmness: Good.
Berry flavor and texture: Initially tart, developing a slight sweetness.
Storage quality: Average.
Suitability for mechanical harvesting: Not suitable.
Uses: Primarily as an edible ornamental and for home gardening.

SEED

Seed abundance in fruit: High.
Seed color: Greyed-Orange RHS 165B.
Seed dry weight: 59.9 mg per 100 seeds.
Seed size: 1.2 to 1.8 mm long.

What is claimed is:

1. A new and distinct variety of blueberry hybrid plant named 'T-885', substantially as illustrated and described herein.

* * * * *